United States Patent [19]
Xu et al.

[11] Patent Number: 5,786,195
[45] Date of Patent: Jul. 28, 1998

[54] **METHOD FOR CLONING AND PRODUCING THE BSSHII RESTRICTION ENDONUCLEASE IN *E. COLI***

[75] Inventors: Shuang-yong Xu, Lexington; Jian-ping Xiao, Wenham, both of Mass.

[73] Assignee: New England Biolabs, Inc., Beverly, Mass.

[21] Appl. No.: 815,688

[22] Filed: Mar. 12, 1997

[51] Int. Cl.$^6$ .................... C12N 9/22; C12N 15/55
[52] U.S. Cl. .................. 435/199; 435/252.3; 435/320.1; 435/252.33; 536/23.2
[58] Field of Search .................. 435/320.1, 252.3, 435/252.33, 199; 536/23.2

[56] References Cited

U.S. PATENT DOCUMENTS

| | | | |
|---|---|---|---|
| 5,200,333 | 4/1993 | Wilson | 435/122.3 |
| 5,498,535 | 3/1996 | Fomenkov | 435/122.3 |

OTHER PUBLICATIONS

Kosykh, et al., Molec. Gen. Genet. 178:717–718 (1980).
Mann, et al., Gene, 3:97–112 (1978).
Walder, et al., Proc. Nat. Acad. Sci., 78:1503–1507 (1981).
Bougueleret, et al., Nucl. Acid Res., 12:3659–3676 (1984).
Gingeras and Brooks, Proc. Nat. Acad. Sci., 80:402–406 (1983).
Theriault and Roy, Gene, 19:355–359 (1982).
Blumenthal, et al., J. Bacteriol., 164:501–509 (1985).
Kiss, et al., Nuc. Acid Res., 13:6403–6421 (1985).
Szomolanyi, et al., Gene, 10:219–225 (1980).
Janulaitis, et al., Gene, 20:197–204 (1982).
Kiss and Baldauf, Gene, 21:111–119 (1983).
Walder, et al., J. Biol. Chem., 258:1235–1241 (1983).
Fomenkov, et al., Nuc. Acid Res. 22:2399–2403 (1994).
Raleigh and Wilson, Proc. Nat. Acad. Sci., 83:9070–9074 (1986).
Schumann, et al., Gene, 157:103–104 (1995).
Roberts and Macelis, Nucleic Acids Research, 24:223–235 (1996).
Xu, S–Y, et al.(1997) Nucl. Acids Res. 25(20), 3991–3994.
Schumann, J., et al. (1995) Gene 157, 103–104.
Schumann, J., et al. (1996) J. Mol. Biol. 257, 949–959.

*Primary Examiner*—Charles L. Patterson, Jr.
*Attorney, Agent, or Firm*—Gregory D. Williams

[57] ABSTRACT

The present invention relates to cloning recombinant DNA molecules encoding a multi-specific methylase gene (bssHIIM1), BssHII restriction endonuclease gene (bssHIIR), and the cognate BssHII methylase gene (bssHIIM2) from *Bacillus stearothermophilus* H3 *E. coli*. The BssHII multi-specific methylase gene was first cloned in a Sau3AI library using a modified pLITMUS28 vector (New England Biolabs, Inc., Beverly, Mass.) with two BssHII sites. Expression of the multi-specific BssHII methylase renders the two BssHII sites resistant to BssHII digestion. Surprisingly, the cloned methylase also modifies some other sites in addition to BssHII site (5'GCGCGC3'). The methylase also modifies BsrFI site (5'RCCGGY3') and HaeII site (5'RGCGCY3'); and partially modifies EagI site (5'CGGCCG3') and MluI site (5'ACGCGT3'). The beginning of the bssHIIR gene was cloned by using two degenerate primers based on the N-terminal amino acid sequence in PCR. The rest of the bssHIIR gene was cloned by inverse PCR. The cognate bssHIIM2 gene was cloned by inverse PCR and PCR. The BssHII restriction endonuclease gene was expressed in *E. coli* host ER417 carrying three plasmids pLysP, pLG-BssHIIM2, pET21AT-BssHIIR.

6 Claims, 6 Drawing Sheets

FIG. 1A

```
          10                    30                    50
ATGACGTTCGACGTAACGCCACAATTACCGGACAGCGGCCTGACCGTCGCGGAACTATTC
MetThrPheAspValThrProGlnLeuProAspSerGlyLeuThrValAlaGluLeuPhe
          70                    90                   110
GCAGGGGGCGGTCTAATGGCGGTCGGCCTCCGCGCTGCCGGTTACAATCTCGTATGGCC
AlaGlyGlyGlyLeuMetAlaValGlyLeuArgAlaAlaGlyTyrAsnLeuValTrpAla
         130                   150                   170
AACGACTTCGATAAGTCGGCTTGCGCCGCCTACCGCCATAATCTCGGCGACCACATCGTA
AsnAspPheAspLysSerAlaCysAlaAlaTyrArgHisAsnLeuGlyAspHisIleVal
         190                   210                   230
CACGGCGACATTACCGCGATTGATCCCGCTGACATTCCGGACACCGACGTGATTGCCGGT
HisGlyAspIleThrAlaIleAspProAlaAspIleProAspThrAspValIleAlaGly
         250                   270                   290
GGCCCGCCTTGTCAGGATTACAGCGTCGCGGGAACCGGTGCGGGCGAAGAGGGCGAACGC
GlyProProCysGlnAspTyrSerValAlaGlyThrGlyAlaGlyGluGluGlyGluArg
         310                   330                   350
GGCAAGCTCGTGTGGGCGTACCTGCGGATTATCGAGGCGAAGCGTCCGAAAGCGTTCATA
GlyLysLeuValTrpAlaTyrLeuArgIleIleGluAlaLysArgProLysAlaPheIle
         370                   390                   410
TTCGAGAACGTGAAGGGTCTCATTACGAAAAAGCACCGCCCGACATTCGATGCGTTGCTG
PheGluAsnValLysGlyLeuIleThrLysLysHisArgProThrPheAspAlaLeuLeu
         430                   450                   470
AAACAATTTAAGATAATCGGGTATAACGTGTCATGGAAACTCATCAACGCATGGGACTAC
LysGlnPheLysIleIleGlyTyrAsnValSerTrpLysLeuIleAsnAlaTrpAspTyr
         490                   510                   530
GGAGTGGCGCAGAAGAGGGAGCGTGTGTTCATCGTGGGCATCCGCGCTGATCTAGGATTT
GlyValAlaGlnLysArgGluArgValPheIleValGlyIleArgAlaAspLeuGlyPhe
         550                   570                   590
GCGTTTGAGTTTCCGGAACCGCGACCGGGGGACTACCGGACGCAAGTGCTGCGCGATGTG
AlaPheGluPheProGluProArgProGlyAspTyrArgThrGlnValLeuArgAspVal
         610                   630                   650
ATCGGGGATTTGCCGGAGCCGGTCGATACTTGCGGCCGACGCGTGAAGAAGGTGGAACGT
IleGlyAspLeuProGluProValAspThrCysGlyArgArgValLysLysValGluArg
         670                   690                   710
GTCGCGGACATGAACGAGCCGGGGCCGACGGTGACGACACAGTTCCGTTGTCAGACGGTC
ValAlaAspMetAsnGluProGlyProThrValThrThrGlnPheArgCysGlnThrVal
         730                   750                   770
GAGATTACGAATCACAACGGGGGAGTCCCGGCGAAAGAATATCCCGGTCACACTGCGTCG
GluIleThrAsnHisAsnGlyGlyValProAlaLysGluTyrProGlyHisThrAlaSer
         790                   810                   830
AGTCTCGAAGGACCAGCGAAAACGATTGTGGCGGGCGCAAACGGCGTGCCCGGCGGCGCG
SerLeuGluGlyProAlaLysThrIleValAlaGlyAlaAsnGlyValProGlyGlyAla
         850                   870                   890
AATTGTTTCTATCCGAACCACGAACGCAAAGAAATCAGCGAAAAGGCGCTCGCAGGCTAC
AsnCysPheTyrProAsnHisGluArgLysGluIleSerGluLysAlaLeuAlaGlyTyr
         910                   930                   950
GAACGGCGCGGAGGACAGGGTGGATTTGGATTCCGCGTGAACCAATGGGACGATCCGTCG
GluArgArgGlyGlyGlnGlyGlyPheGlyPheArgValAsnGlnTrpAspAspProSer
```

FIG. 1B

```
         970                990                1010
CCTACGATATTCGGCCGGATTTTTAACGAAGGAAAGGCGTTCGTCCATCCGGGGCCTATC
ProThrIlePheGlyArgIlePheAsnGluGlyLysAlaPheValHisProGlyProIle
         1030               1050               1070

GAAAATCACGATGAAAAATCGTTCTGGACGCCAAAATCCGAATACACCTACGACCAAGCT
GluAsnHisAspGluLysSerPheTrpThrProLysSerGluTyrThrTyrAspGlnAla
         1090               1110               1130

AATCGTGTACAGTCGTGGGATAAGCCAAGTGCCACAATCCCCGCGCATCACAACAGTGGA
AsnArgValGlnSerTrpAspLysProSerAlaThrIleProAlaHisHisAsnSerGly
         1150               1170               1190

CAGCCGAATCATCCGCAGTACGCGAACCACGACCGGTACGCTGTCCTCGCGAAGGACAGC
GlnProAsnHisProGlnTyrAlaAsnHisAspArgTyrAlaValLeuAlaLysAspSer
         1210               1230               1250

GACGTGATTCCGAAAATCCCCGAAGGAGCGTCGAATCGACAAGCCGCAAAGATAGAACCG
AspValIleProLysIleProGluGlyAlaSerAsnArgGlnAlaAlaLysIleGluPro
         1270               1290               1310

GACATTTATTGGTCGGACTATATCCGGGAGAGTCGCGAAAACCCTGCACGCACAATGATC
AspIleTyrTrpSerAspTyrIleArgGluSerArgGluAsnProAlaArgThrMetIle
         1330               1350               1370

GGTACAGGTAAGCCGAAGATTCACCCGACACAGCCCCGCCGTTTCACTGTCCGCGAGTGC
GlyThrGlyLysProLysIleHisProThrGlnProArgArgPheThrValArgGluCys
         1390               1410               1430

CTGCGGATTCAATCGGTGCCCGACTGGTACGTGCTGCCGGATGACATTTCGCTATCCGCG
LeuArgIleGlnSerValProAspTrpTyrValLeuProAspAspIleSerLeuSerAla
         1450               1470               1490

CAATACCGTATCGTCGGCAACGGGATAGCGTCGCGCGTCGCGTACTTGCTCGGAATTGCC
GlnTyrArgIleValGlyAsnGlyIleAlaSerArgValAlaTyrLeuLeuGlyIleAla
         1510               1530               1550

CTGGCGGAACAACTCCGTGCCGCAACGGAATCGAGCGCAATAGGCGAGCGTTTGATTGCG
LeuAlaGluGlnLeuArgAlaAlaThrGluSerSerAlaIleGlyGluArgLeuIleAla
         1570               1590

GATAATACGGACGACTGCGCCAACAGTCGGAAGGAGGCGGTCTAG
AspAsnThrAspAspCysAlaAsnSerArgLysGluAlaValEnd
```

FIG. 2A

```
            10                    30                    50
            .                     .                     .
ATGGGAGAAAACCAAGAATCAATATGGGCAAATCAGATATTGGACAAGGCCCAACTGGTT
MetGlyGluAsnGlnGluSerIleTrpAlaAsnGlnIleLeuAspLysAlaGlnLeuVal
            70                    90                   110
            .                     .                     .
ATGCCAGAAACTCATGAACAAAATTTAGCTGATACTTTGATTGACTTATGTTACAATGCA
MetProGluThrHisGluGlnAsnLeuAlaAspThrLeuIleAspLeuCysTyrAsnAla
           130                   150                   170
            .                     .                     .
GCAAAGAGAACTAATGTTCCCGTCGGAATTGCTCTGGCTGCATCATTCGATTTATTGGTA
AlaLysArgThrAsnValProValGlyIleAlaLeuAlaAlaSerPheAspLeuLeuVal
           190                   210                   230
            .                     .                     .
GGAGCCGAGTATTATAGAAACGTAATCAACAGAGGGTGGTGTTACTGTCCAGAACACCAA
GlyAlaGluTyrTyrArgAsnValIleAsnArgGlyTrpCysTyrCysProGluHisGln
           250                   270                   290
            .                     .                     .
TCTTTAATTTTCCCTTATACAAATACTTGCCCTGCATGTGTACTTTCGGGAAAATTTCAT
SerLeuIlePheProTyrThrAsnThrCysProAlaCysValLeuSerGlyLysPheHis
           310                   330                   350
            .                     .                     .
TTTCATCGTTCTAATAAACCGGAATCGGGGAAAATCGGTACGGCAACTTCCCGCTTGCTT
PheHisArgSerAsnLysProGluSerGlyLysIleGlyThrAlaThrSerArgLeuLeu
           370                   390                   410
            .                     .                     .
TGCGTATTTCTGGACAGGCTTTTTGTAAAATCATCAAGGAACTTTAAGATTTTCAAAGGC
CysValPheLeuAspArgLeuPheValLysSerSerArgAsnPheLysIlePheLysGly
           430                   450                   470
            .                     .                     .
AGTGAACCTATTGATATTTTAATACACGATGAGCAGAAAAACATAATGCTATTGGCTGAA
SerGluProIleAspIleLeuIleHisAspGluGlnLysAsnIleMetLeuLeuAlaGlu
           490                   510                   530
            .                     .                     .
GTTAAAGCTGCTCCGCTAATTACCTTACCATTATTGGTtCGATCTGAAGAAAAAATTACC
ValLysAlaAlaProLeuIleThrLeuProLeuLeuValArgSerGluGluLysIleThr
           550                   570                   590
            .                     .                     .
GATTTAGTCGATGGTGAAATAGTTGAAATACCACATTCTGCCGTAGACAACTCATCTTTA
AspLeuValAspGlyGluIleValGluIleProHisSerAlaValAspAsnSerSerLeu
           610                   630                   650
            .                     .                     .
TCTTCATCAAATATTTGCTTGCTTCTCCCTGTTTTTCATGATGGGAGTTGGCAAAGTAAA
SerSerSerAsnIleCysLeuLeuLeuProValPheHisAspGlySerTrpGlnSerLys
           670                   690                   710
            .                     .                     .
TTTGTTGAACTTCAAACGAAAGATGATATATTAACAAATACCATTTGGGCATACGGCCAG
PheValGluLeuGlnThrLysAspAspIleLeuThrAsnThrIleTrpAlaTyrGlyGln
           730                   750                   770
            .                     .                     .
CTAGAAAATATTTTTAGGGGAAATAATGATCTTTTTGATTTATACTTAGATACTTGGAAA
LeuGluAsnIlePheArgGlyAsnAsnAspLeuPheAspLeuTyrLeuAspThrTrpLys
           790                   810                   830
            .                     .                     .
AGGGCATTCGAAGCATATCAGGTGGCTTATCACGAAAAAGATAGATCAAGCAACATTTTT
ArgAlaPheGluAlaTyrGlnValAlaTyrHisGluLysAspArgSerSerAsnIlePhe
           850                   870                   890
            .                     .                     .
TGGTTGACAAATGCTTGTGGACAACCTGAGCCAAGACCTGTCGATTGGCCCGCTAGATCG
TrpLeuThrAsnAlaCysGlyGlnProGluProArgProValAspTrpProAlaArgSer
           910                   930                   950
            .                     .                     .
GGAACAGGTTATGAATCTGTTTCTGATGGAAAAACTAgTGTGGGCaTGGATAGAACTGAC
GlyThrGlyTyrGluSerValSerAspGlyLysThrSerValGlyMetAspArgThrAsp
```

FIG. 2B

```
           970                 990                1010
             .                  .                   .
GATATTAAAAAAGGAATTTATCAAGTGTTAAAGCTGGGCGCTGAGAGTAAGCCCATAAAC
AspIleLysLysGlyIleTyrGlnValLeuLysLeuGlyAlaGluSerLysProIleAsn
          1030                1050                1070
             .                  .                   .
CAGCAGTATCAAATTAAAACAGCACTAATATCAAATATTCATGCCGCGAGACACTACGAC
GlnGlnTyrGlnIleLysThrAlaLeuIleSerAsnIleHisAlaAlaArgHisTyrAsp
          1090                1110                1130
             .                  .                   .
GAATATCTAACCTCATTGCAAGATGTAGTTTGGGCATTAGATGAAACAGGATTAGCTAAG
GluTyrLeuThrSerLeuGlnAspValValTrpAlaLeuAspGluThrGlyLeuAlaLys
          1150                1170                1190
             .                  .                   .
AAAGCAGGTGAACTTGACAGTGAGACACCAATCTACAACTTATTTGACGGAATCATTTCC
LysAlaGlyGluLeuAspSerGluThrProIleTyrAsnLeuPheAspGlyIleIleSer
          1210                1230                1250
             .                  .                   .
TTTACGCGAAATCACCCTAGAGATGAATGGATTAGAGAAAACTTCCAATTCTGA
PheThrArgAsnHisProArgAspGluTrpIleArgGluAsnPheGlnPheEnd
```

FIG. 3

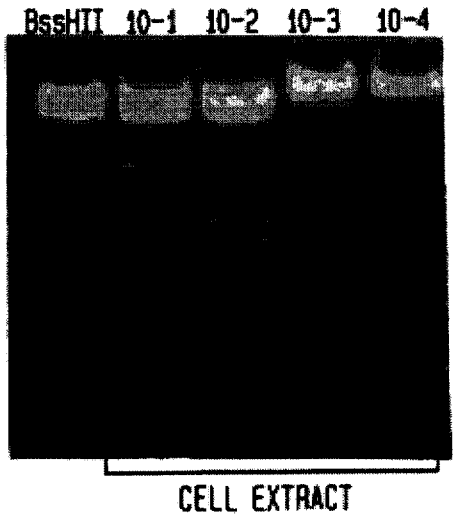

CELL EXTRACT

FIG. 4A

```
            10                    30                    50
             .                     .                     .
ATGAATGGATTAGAGAAAACTTCCAATTCTGACGAATCTTTCGACTTTGTTTTTAATCAT
MetAsnGlyLeuGluLysThrSerAsnSerAspGluSerPheAspPheValPheAsnHis
            70                    90                   110
             .                     .                     .
GTCTTTCGTCGCTCAGGTTCTGAAGTACAAAAAAGAATTGATGCACTAAAAATCGGTCAA
ValPheArgArgSerGlySerGluValGlnLysArgIleAspAlaLeuLysIleGlyGln
           130                   150                   170
             .                     .                     .
AAAATGCAAGACCTGCCTGAAGAACTATGGCATGACAGCTTTCGTTATTATGTAAAGGAA
LysMetGlnAspLeuProGluGluLeuTrpHisAspSerPheArgTyrTyrValLysGlu
           190                   210                   230
             .                     .                     .
GACCCAAATAGACGCGGCGGCCCAAACATGCGAATGATACGCCTTGATCCGTCTAAACCT
AspProAsnArgArgGlyGlyProAsnMetArgMetIleArgLeuAspProSerLysPro
           250                   270                   290
             .                     .                     .
TCTCTAACGGTGACAGGATATATTTTCAATAAGTTTGTGCATCCTTATGAGAACCGTTTT
SerLeuThrValThrGlyTyrIlePheAsnLysPheValHisProTyrGluAsnArgPhe
           310                   330                   350
             .                     .                     .
ATTACCGTGCGTGAAGCTGCAAGACTGCAAGGCTTCCCAGATTCATTAAAATTTGAAGGC
IleThrValArgGluAlaAlaArgLeuGlnGlyPheProAspSerLeuLysPheGluGly
           370                   390                   410
             .                     .                     .
TCATTAACTAGTACGCAGATGCAAGTCGGCAATGCCGTGCCAGTACAATTAGCTAAAGCA
SerLeuThrSerThrGlnMetGlnValGlyAsnAlaValProValGlnLeuAlaLysAla
           430                   450                   470
             .                     .                     .
GTTTTTGAAGCGGTACTAATTTCTGTTAGAAAATTAGGATATGGCAAAAGAAATTTAACT
ValPheGluAlaValLeuIleSerValArgLysLeuGlyTyrGlyLysArgAsnLeuThr
           490                   510                   530
             .                     .                     .
GCGTTTAGTCTTTTTAGCGGTGCTGGTGGACTTGATATTGGTGCTGAACAAGCTACATAT
AlaPheSerLeuPheSerGlyAlaGlyGlyLeuAspIleGlyAlaGluGlnAlaThrTyr
           550                   570                   590
             .                     .                     .
AAATCAATGAAAATAGAAACCTTCGTGACATTAGATAATTGGAAAGACGCTTGTGATACC
LysSerMetLysIleGluThrLeuValThrLeuAspAsnTrpLysAspAlaCysAspThr
           610                   630                   650
             .                     .                     .
CTTAGAGGATTCTATCAAGGACGTACAAGTGTTTTGCAAGGAGATATTTCAGAGATACAA
LeuArgGlyPheTyrGlnGlyArgThrSerValLeuGlnGlyAspIleSerGluIleGln
           670                   690                   710
             .                     .                     .
GACCCCAAATTATTATGGCATCAAGAATCACAACACGATCAGATTCCTGATATTGTATTT
AspProLysLeuLeuTrpHisGlnGluSerGlnHisAspGlnIleProAspIleValPhe
           730                   750                   770
             .                     .                     .
GGGGGGCCTCCCTGCCAGGCGTTCAGTCAAGCTGGTAAACAAAAGGCAACAAATGACCCG
GlyGlyProProCysGlnAlaPheSerGlnAlaGlyLysGlnLysAlaThrAsnAspPro
           790                   810                   830
             .                     .                     .
AGAGGAAACTTGATTTACGAGTACCTCAGATTTATTGAGAAAATCAACCCTCCATTCTTT
ArgGlyAsnLeuIleTyrGluTyrLeuArgPheIleGluLysIleAsnProProPhePhe
           850                   870                   890
             .                     .                     .
GTAATGGAAAATGTAGCGAACTTGAAAGGTGTTCAGCGCGGGGAACTTTATCAAGACATT
ValMetGluAsnValAlaAsnLeuLysGlyValGlnArgGlyGluLeuTyrGlnAspIle
           910                   930                   950
             .                     .                     .
TTGGAGCGCATGTCTAATCTTGGTTATAATGTGACGGTTGCCCCGCTTCTTGCGGCGGAT
LeuGluArgMetSerAsnLeuGlyTyrAsnValThrValAlaProLeuLeuAlaAlaAsp
```

FIG. 4B

```
              970                    990                   1010
               .                      .                     .
TATGGTGCACCACAGCTTAGAAAACGTCTAATATTCTTAGGCTGTAAAAAGGAATTCGGG
TyrGlyAlaProGlnLeuArgLysArgLeuIlePheLeuGlyCysLysLysGluPheGly
              1030                   1050                  1070
               .                      .                     .
GTGATGGAACTCCCAGTTCCGACCCATAGTAATACACCCGATTTATTATCACCAAACCCT
ValMetGluLeuProValProThrHisSerAsnThrProAspLeuLeuSerProAsnPro
              1090                   1110
               .                      .
TATGTAACAGTGGGGAAGCCTTCAAAGGTTTACCTAAACTTGTTTAA
TyrValThrValGlyGluAlaPheLysGlyLeuProLysLeuValEnd
```

FIG. 5

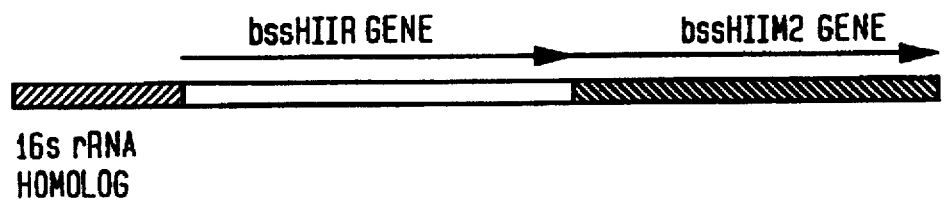

METHOD FOR CLONING AND PRODUCING THE BSSHII RESTRICTION ENDONUCLEASE IN *E. COLI*

BACKGROUND OF THE INVENTION

The present invention relates to recombinant DNA which encodes the BssHII restriction endonuclease as well as BssHII methylase, and the production of BssHII restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, *Nucl. Acids Res.* 24:223–235, (1996)).

Bacteria tend to possess at most, only a small number of restriction endonucleases per species. The endonucleases typically are named according to the bacteria from which they are derived. Thus, the species *Deinococcus radiophilus* for example, produces three different restriction endonucleases, named DraI, DraII and DraIII. These enzymes recognize and cleave the sequences 5'TTTAAA3', 5'PuGGNCCPy3' and 5'CACNNNGTG3' respectively. *Escherichia coli* RY13, on the other hand, produces only one enzyme, EcoRI, which recognizes the sequence 5' GAATTC3'.

It is thought that in nature, restriction endonucleases play a protective role in the welfare of the bacterial cell. They enable bacteria to resist infection by foreign DNA molecules like viruses and plasmids that would otherwise destroy or parasitize them. They impart resistance by cleaving invading foreign DNA molecule each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one particular nucleotide within the sequence by the addition of a methyl group. Following methylation, the recognition sequence is no longer cleaved by the restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet.* 178: 717–719, (1980); HhaII: Mann et al., *Gene* 3:97–112, (1978); PstI: Walder et al., *Proc. Nat. Acad. Sci.* 78:1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12:3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985)).

A third approach, and one that is being used to clone a growing number of systems, is for an active methylase gene (Wilson, U.S. Pat. No. 5,200,333 issued Apr. 6, 1993 and BsuRI: Kiss et al., *Nucl. Acid. Res.* 13:6403–6421, (1985)).

Since restriction and modification genes are often closely linked, both genes can often be cloned simultaneously. However, this selection does not always yield a complete restriction system, but instead yields only the methylase gene (BspRI: Szomolanyi et al., *Gene* 10:219–225, (1980); BcnI: Janulaitis et al., *Gene* 20:197–204 (1982); BsuRI: Kiss and Baldauf, *Gene* 21:111–119, (1983); and MspI: Walder et al., *J. Biol. Chem.* 258:1235–1241, (1983)).

A more recent method, the "endo-blue method", has been described for direct cloning of restriction endonuclease genes in *E. coli* based on the indicator strain of *E. coli* containing the dinD::lacZ fusion (Fomenkov et al., U.S. Pat. No. 5,498,535, issued Mar. 12, 1996; Fomenkov et al., *Nucl. Acids Res.* 22:2399–2403, (1994)). This method utilizes the *E. coli* SOS response following DNA damage caused by restriction endonucleases or non-specific nucleases. A number of thermostable nuclease genes (Tth111I, BsoBI, Tf nuclease) have been cloned by this method.

Another obstacle to cloning these systems in *E. coli* was discovered in the process of cloning diverse methylases. Many *E. coli* strains (including those normally used in cloning) have systems that resist the introduction of DNA containing cytosine methylation. (Raleigh and Wilson, *Proc. Natl. Acad. Sci., USA* 83:9070–9074, (1986)). Therefore, it is also necessary to carefully consider which *E. coli* strain(s) to use for cloning.

Because purified restriction endonucleases and modification methylases, are useful tools for creating recombinant molecules in the laboratory, there is a commercial incentive to obtain bacterial strains through recombinant DNA techniques that produce these enzymes in large quantities. Such overexpression strains would also simplify the task of enzyme purification.

SUMMARY OF THE INVENTION

The present invention relates to recombinant DNA molecules encoding a multi-specific methylase gene (bssHIIM1), BssHII restriction endonuclease gene (bssHIIR), and the cognate BssHII methylase gene (bssHIIM2) from *Bacillus stearothermophilus* H3 *E. coli*. The BssHII multi-specific methylase gene was first cloned in a Sau3AI library using a modified pLITMUS28 vector (New England Biolabs, Inc., Beverly, Mass.) with two BssHII sites. Expression of the multi-specific BssHII methylase renders the two BssHII sites resistant to BssHII digestion. Surprisingly, the cloned methylase also modifies some other sites in addition to BssHII site (5'GCGCGC3'). Specifically, this methylase also modifies BsrFI (5'RCCGGY3') and HaeII sites (5'RGCGCY3'); and partially modifies EagI (5'CGGCCG3') and MluI sites (5'ACGCGT3'). No mono-specific BssHII methylase was recovered from the partial Sau3AI libraries prepared from *B. stearothermophilus* H3 genomic DNA.

To facilitate the cloning of BssHII restriction endonuclease gene, large amounts of BssHII restriction endonuclease protein was purified from *B. stearothermophilus* H3 cells. The N-terminal amino acid sequence was determined as follows: (Met) Gly Glu Asn Gln Glu Ser Ile Trp Ala Asn Gln Ile Leu Asp Lys Ala Gln Leu Val Ser? Pro Glu Thr His Xaa Gln Asn? Xaa Ala Asp (SEQ ID NO:1). (?=ambiguous calling).

DNA fragments adjacent to the multi-specific BssHII methylase gene (bssHIIM1) were sequenced in the hope of finding BssHII endonuclease gene. Over 5000 bp of DNA surrounding the multi-specific methylase gene was sequenced. Translation of the open reading frames into amino acid sequences did not match the N-terminal amino acid sequence of the BssHII endonuclease protein. It was concluded that the bona fide BssHII restriction endonuclease gene was likely located somewhere else in the *B. stearothermophilus* H3 chromosome.

In order to determine the location of the BssHII restriction endonuclease genes, two sets of degenerate primers were designed based on the protein sequence and used in PCR to amplify the first 59 bp of the BssHII restriction endonuclease gene from *B. stearothermophilus* H3 genomic DNA which was then cloned into pUC19 (ATCC 37254) and the insert was sequenced. A set of inverse PCR primers was designed from the known 59 bp sequence. An inverse PCR product was found in the Sau3AI digested and self-ligated *B. stearothermophilus* H3 genomic DNA. The inverse PCR DNA was cloned and sequenced. This provided an additional 465 bp of new DNA coding sequence. Another set of inverse PCR was designed from the end of the 465 bp sequence and used to amplify the remaining part of the BssHII endonuclease gene from HinfI or RsaI cleaved and self-ligated *B. stearothermophilus* H3 genomic DNA. The inverse PCR products were cloned and sequenced. After another 730 bp of new sequence, a stop codon was found in the RsaI fragment. The entire BssHII endonuclease gene (bssHIIR) is 1254 bp (59 bp+465 bp+730 bp), encoding the 417-aa BssHII restriction endonuclease with predicted molecular mass of 47 kDa.

To premodify *E. coli* chromosome, the multi-specific BssHII methylase gene (bssHIIM1) was cloned in a compatible vector pACYC184 (ATCC 37033). The BssHII endonuclease gene was amplified by PCR. An efficient ribosome binding site and an optimal spacing was engineered in front of bssHIIR gene. The PCR product were cloned into pUC19. Three isolates carrying the PCR inserts were found. However, no activity was detected in the IPTG-induced cell cultures. It was concluded that the three inserts may have carried mutations in the bssHIIR gene.

Vector pUC19 is a high-copy-number plasmid containing the lac promotor. Expression of genes from the lac promotor is not tightly regulated. Therefore, it was reasoned that a tightly-regulated promotor such as the T7 promotor might be desirable for the expression of bssHIIR gene. The bssHIIR gene was amplified by PCR with primers flanked by XbaI and BamHI sites. An efficient ribosome binding site and an optimal spacing were engineered in front of the gene. The PCR product was ligated into vector pET21AT (New England Biolabs Inc., Beverly, Mass.), a T7 expression vector with transcription terminators upstream of the T7 promoter. The bssHIIM1 gene was first inserted into the vector pLG339. The endonuclease-carrying plasmid was then transformed into *E. coli* cell ER2504 [pLysS, pLG-BssHIIM1]. *E. coli* cells carrying pLysS, pLG-BssHIIM1 and pET21AT-BssHIIR were induced with IPTG and cell extracts were assayed for BssHII endonuclease activity. Cell extracts from twelve isolates were assayed and all twelve clones produced BssHII endonuclease activity. One example is shown in FIG. 4.

Since type II restriction endonuclease gene and the cognate methylase gene are located in close proximity to each other, a set of inverse PCR primers were synthesized based on the end of restriction endonuclease sequence. Downstream sequences were amplified by inverse PCR and cloned. The bona fide BssHII methylase gene (bssHIIM2) was cloned in two steps of inverse PCR. The entire bssHIIM2 gene was amplified by PCR and cloned into a compatible vector pLG339 (ATCC 37131) derived from pSC101 to premodify *E. coli* chromosome. The premodified host ER2417 [pLysP, pLG-BssHIIM2] was transformed with pET21AT-BssHIIR. The resulting strain ER2417 [pLysP, pLG-BssHIIM2, pET21AT-BssHIIR] produced $1 \times 10^5$ units of BssHII restriction endonuclease after IPTG induction.

BRIEF DESCRIPTION OF THE FIGURES

FIG. 1 is the DNA sequence of the multi-specific BssHII gene (bssHIIM1) and its encoded amino acid sequence (SEQ ID NO:2).

FIG. 2 is the DNA sequence of the BssHII restriction endonuclease gene (bssHIIR) and its encoded amino acid sequence (SEQ ID NO:3).

FIG. 3 is the BssHII endonuclease activity assay using cell extract and λ DNA.

FIG. 4 is the DNA sequence of the bona fide BssHII methylase gene (bssHIIM2) and its encoded amino acid sequence (SEQ ID NO:4).

FIG. 5 is the gene organization of the BssHII restriction modification system.

DETAILED DESCRIPTION OF THE INVENTION

The method described herein by which the multi-specific BssHII methylase gene and the BssHII restriction endonuclease and the cognate methylase gene are preferably cloned and expressed using the following steps:

1. The genomic DNA of *B. stearothermophilus* H3 is purified.

2. The DNA is digested partially with a restriction endonuclease such as Sau3AI, or any of its isoschizomers, that generates a DNA fragment(s) containing the entire BssHII multi-specific methylase gene. Alternatively, one can skip to step 9 to clone the BssHII endonuclease gene directly by PCR and inverse PCR using degenerate primers that are designed from the N-terminus amino acid sequence.

3. The Sau3AI-digested genomic DNA is then ligated into BamHI-cleaved/CIP treated pLITMUS cloning vector with two BssHII sites. The ligated DNA is used to transform an appropriate host, i.e. a HsdR−, McrBC−, Mrr− strain, such as E. coli strain RR1. The DNA/cell mixtures are then plated on ampicillin media selecting for transformed cells. After incubation, the transformed colonies are harvested and amplified to form the primary cell library.

4. The recombinant plasmids are next purified in toto from the primary cell library to make the primary plasmid library. The purified plasmid library is then digested to completion in vitro with BssHII restriction endonuclease, or any BssHII isoschizomer. The BssHII endonuclease digestion causes the selective destruction of unmodified, non-methylase-containing clones, resulting in an increase in the relative frequency of BssHII methylase-carrying clones.

5. Identification of the multi-specific BssHII methylase clone: The digested plasmid library DNA is transformed back into a host such as E. coli strain RR1 and transformed colonies are again obtained by plating on ampicillin plates. The colonies are picked and their plasmids are prepared and analyzed for the presence of the BssHII methylase gene by incubating purified plasmid DNA in vitro with BssHII endonuclease to determine whether it is resistant to BssHII digestion.

6. Once it has been established that the methylase gene has been cloned, the clone is analyzed by restriction mapping and deletion mapping. The entire insert is then sequenced. Following this approach, one open reading frame corresponding to the BssHII multi-specific methylase gene is found. The cloned methylase also modifies some other sites in addition to BssHII site (5'GCGCGC3'). The plasmid DNA carrying the multi-specific BssHII methylase gene is also resistant to BsrFI (5'RCCGGY3') and HaeII (5'RGCGCY3') digestion; and is partially resistant to EagI (5° CGGCCG3') and MluI (5'ACGCGT3') digestion. It is concluded that the cloned methylase is a multi-specific methylase.

7. BssHII restriction endonuclease protein is purified in large quantities and the N-terminus amino acid sequence determined. The N-terminus sequence is as following (Met) Gly Glu Asn Gln Glu Ser Ile Trp Ala Asn Gln Ile Leu Asp Lys Ala Gln Leu Val Ser? Pro Glu Thr His Xaa Gln Asn? Xaa Ala Asp (SEQ ID NO:1). (?=ambiguous calling).

8. Based on the above approach, a 5.8 kb DNA fragment surrounding the multi-specific BssHII methylase gene is sequenced using methylase containing clones. The DNA sequence is translated in all six frames and compared to the amino acid sequence of BssHII restriction endonuclease. However, no apparent identity/homology is found between the translated amino acid sequences and the N-terminus amino acid sequence of the purified BssHII restriction endonuclease. It is concluded that the true BssHII restriction endonuclease gene is not located next to the multi-specific methylase.

9. Efforts are made to clone the BssHII endonuclease directly by PCR and inverse PCR based on the N-terminus amino acid sequence. Two sets of degenerate primers are designed from the first five amino acid residues (MGENQE) (SEQ ID NO:5) and residues 15 to 20 (DKAQLV) (SEQ ID NO:6). The primers are used to amplify the beginning 59 bp of the BssHII restriction endonuclease gene from the B. stearothermophilus H3 genomic DNA by PCR. Multiple PCR products are found and DNA fragments in the range of 59–67 bp are gel-purified and cloned into pUC19 and sequenced. One of the two clones contained translated amino acid sequence that is identical to the expected N-terminus amino acid sequence.

10. Inverse PCR primers are designed from the beginning 59 bp DNA and used to amplify surrounding DNA sequences from B. stearothermophilus H3 genomic DNA by inverse PCR. B. stearothermophilus H3 genomic DNA is digested with the following restriction enzymes with 6 bp recognition sequences: AatII, BamHI, BglII, BspEI, ClaI, EcoRI, HindIII, MluI, NheI, or SphI and restriction enzymes with 4–5 bp recognition sequences: Sau3AI, NlaIII, MspI, MboI, HinPlI, HhaI, HpaII, HaeII, EaeI, or AciI. The digestions give rise to reasonable size template DNA (less than 10 kb) for inverse PCR reaction. The digested DNA samples are self-ligated at a low DNA concentration (less than 2 microgram per ml). The ligated circular DNA is used as templates for inverse PCR reactions. Single PCR products are found in Sau3AI, MboI, and AciI digested and self-ligated genomic DNA. The DNA fragments are cloned into pUC19 and sequenced, which gives rise to 465 bp of new sequence.

11. Inverse PCR primers are designed from the end of 465 bp new sequence and used to amplify additional surrounding DNA. B. stearothermophilus H3 genomic DNA is digested with ApoI, BsaWI, Sau3AI, NlaIII, MspI, MboI, HinPlI, HhaI, HpaII, HaeII, EaeI, TaiI, HinfI, RsaI, or AciI. The digested DNA samples are self-ligated at a low DNA concentration (less than 2 microgram per ml). The ligated circular DNA is used as templates for inverse PCR reaction. Single inverse PCR products are found in HinfI or RsaI digested and self-ligated genomic DNA. The DNA fragments are cloned and sequenced. After 730 bp of additional sequence, a stop codon is found in the sequenced RsaI fragment. The entire BssHII endonuclease gene is 1254 bp (59 bp+465 bp+730 bp), encoding the 417-aa BssHII endonuclease with predicted molecular mass of 47 kDa.

12. The multi-specific BssHII methylase gene is cloned into pACYC184 (ATCC 37033) to premodify E. coli host. The entire BssHII endonuclease gene is amplified by PCR with two primers. An efficient ribosome binding site and 7 bp spacing are engineered before the ATG start codon. The endonuclease gene is cloned into pUC19. Three clones with inserts are found, but no BssHII activity is found in cell extract of IPTG-induced cell cultures.

13. In a second attempt to express the bssHIIR gene, a T7 expression vector pET21AT is used for tightly-regulated expression (F. W. Studier and B. A. Moffatt, J. Mol. Biol. 189:113–130, (1986)). Vector pET21AT carries four copies of transcription terminators upstream of the T7 promoter. The co-transformation of pLysS (F. W. Studier, J. Mol. Biol. 219:37–44, (1991)) further reduces the basal level expression under non-induced condition. The bssHIIM1 gene is amplified by PCR and cloned into a compatible vector pLG339 (ATCC 37131) derived from pSC101. The bssHIIR gene is amplified by PCR and cloned into pET21AT. E. coli host cell for T7 expression, ER2504, is transformed with pLysS, pLG-BssHIIM1, pET21AT-BssHIIR. Twelve isolates are induced with IPTG and cell extracts are prepared and assayed for BssHII restriction endonuclease activity. All clones produce BssHII endonuclease.

14. To clone the methylase gene adjacent to the bssHIIR gene, a set of primers are made to amplify the downstream DNA sequences. Inverse PCR products are found in the inverse PCR reactions of HhaI, HaeIII, and Sau3AI digested and self-ligated genomic DNA. The inverse PCR products are cloned and sequenced. An unfinished open reading frame is found in the newly derived 895 bp sequence and compared to the known genes in Genbank. This unfinished open reading frame has amino acid sequence similarity to the known $C^5$ methylases.

15. A second set of inverse PCR primers are synthesized and used to amplify the downstream sequences. Inverse PCR products are found in the inverse PCR reactions of StyI digested and self-ligated DNA. The DNA product is cloned into pUC19 and the insert is sequenced. The entire BssHII methylase gene (bssHIIM2) is found to be 1128 bp, encoding the BssHII methylase protein with molecular mass of 42.2 kDa.

16. The entire bssHIIM2 gene is amplified and inserted into pLG339 vector. The pre-modified *E. coli* host cell ER2417 [pLysP, pLG339-BssHIIM2] is transformed with pET21AT-BssHIIR. The resulting strain ER2417 [pLysP, pLG339-BssHIIM2, pET21AT-BssHIIR] (NEB#1070) produces $1\times10^5$ units of BssHII restriction endonuclease per gram of wet *E. coli* cells.

A sample of NEB#1070 has been deposited under the terms and conditions of the Budapest Treaty with the American Type Culture Collection on Feb. 24, 1997 and received ATCC Accession Number 98334.

The present invention is further illustrated by the following Example. The Example is provided to aid in the understanding of the invention and is not construed as a limitation thereof.

The references cited above and below are hereby incorporated by reference.

EXAMPLE I

CLONING OF BSSHII RESTRICTION ENDONUCLEASE GENE

1. Cloning of the multi-specific BssHII methylase gene (bssHIIM1) by using the methylase selection method.

Ten μg of *B. stearothermophilus* H3 genomic DNA was cleaved partially by 4, 2, 1, 0.5, or 0.25 units of Sau3AI at 37° C. for 30 min. The partially digested DNA was analysed by gel electrophoresis. It was found that 1 unit and 0.5 unit of Sau3AL digestion gave rise to limited partial digestion. The Sau3AL partially digested *B. stearothermophilus* H3 genomic DNA was ligated into BamHI cleaved/CIP treated pLITMUS28 (a pUC19 derivative with two BssHII sites, New England Biolabs Inc., Beverly, Mass.) at 16° C. overnight. Ligated DNA was transformed into RR1 competent cells and plated on ampicillin plates. A total of about $1\times10^5$ cells were derived from the transformation experiment. These cells were pooled together and inoculated into 1 liter LB broth plus Ap and cultured overnight at 37° C. Plasmid DNA was prepared from the primary cell library. 10, 5, 2, and 1 μg of plasmid DNA were cleaved with 40 units of BssHII restriction endonuclease for four hours at 50° C. The BssHII-digested DNA was retransformed into RR1 competent cells. Plasmids were isolated again from cultures of the surviving transformants and digested with BssHII restriction enzyme to see if the plasmid DNA was resistant to BssHII digestion. Thirty-six plasmids were checked for resistance to BssHII digestion. Three resistant clones (#3, #18, and #30) were found. They carry about 6 kb genomic DNA insert. When these plasmids were digested with BsrFI, SacII, EagI, MluI, HaeII, NarI, HhaI, SacI, or EcoO109I, it was found that the plasmid DNA was also resistant or partially resistant to BsrFI, HaeII, EagI, or MluI digestions. Cell extracts were prepared from the three isolates and assayed for BssHII endonuclease activity. No apparent BssHII endonuclease activity was detected in the three cell extracts. The entire multi-specific methylase gene and the surrounding DNA were sequenced. The bssHIIM1gene sequence is shown in FIG. 1. No apparent restriction endonuclease gene was found. It was concluded that this methylase gene may be a phage encoded multi-specific methylase gene. The same gene was cloned and its sequence has been published (Schumann, J., et al, *Gene* 157:103–104 (1995)).

2. Cloning of bssHIIR gene.

Since the methylase selection method yielded only a multi-specific BssHII methylase, efforts were concentrated on directly cloning the BssHII endonuclease gene. BssHII restriction endonuclease was purified from *B. stearothermophilus* H3 cells by chromatography and subjected to N-terminal amino acid sequencing. The N-terminal amino acid sequence is as follows:
(Met) Gly Glu Asn Gln Glu Ser Ile Trp Ala Asn Gln Ile Leu Asp Lys Ala Gln Leu Val Ser? Pro Glu Thr His Xaa Gln Asn? Xaa Ala Asp (SEQ ID NO:1) (?=ambiguous calling) (the residues in bold were used to design degenerate primers).

A forward degenerate primer was designed based on the first six amino acid sequence (Met) Gly Glu Asn Gln Glu (SEQ ID NO:5).

The forward primer sequence is as follows:

5' ATGGGNGARAAYCARGA 3' (SEQ ID NO: 7)

(N = A, C, G and T; R = A, G; Y = C, T).

Two reverse degenerate primers were designed based on the amino acid sequence Asp Lys Ala Gln Leu Val (SEQ ID NO:6). Because the codon coding for Leu has six possibilities (CUG, CUC, CUU, CUA, UUG, and UUA), two degenerate primers were made, one with CTN encoding Leu, the other with TTR encoding Leu. The two reverse degenerate primer sequences are:

reverse primer 1:
5' ACYAAYTGNGCYTTRTC 3' (SEQ IF NO:8)
(N = A, C, G AND T; R = A, G; Y = C, T)
reverse primer 2:
5' ACNAGYTGNGCYTTRTC 3' (SEQ ID NO:9)
(N = A, C, G AND T; R = A, G; Y = C, T)

Two PCR reactions were set up: the forward primer and reverse primer 1 were used in PCR reaction 1, and the forward primer and reverse primer 2 were used in PCR reaction 2. A 59 bp PCR product would be expected if the DNA amplification showed positive results. The 59 bp of the BssHII endonuclease gene encode the first 20 amino acids. After 30 rounds of PCR amplification (95° C. 1 min, 40° C. 1 min, 72° C. 30 sec, 30 cycles), an expected PCR product was detected on an agarose gel. The small DNA product was gel-purified through a 3% low melting agarose gel. The gel slice was treated with β-agarase and the DNA was precipitated and cloned into pUC19. Two clones with insert were sequenced. The sequence of the first 59 bp of bssHIIR gene are as follows:

5' ATGGGAGAAAACCAAGAATCAATATGGGCAAATCAGATATTG GACAAGGCCCAACTGGT 3'. (SEQ ID NO:10)

The encoded amino acid sequence is: Met Gly Glu Asn Gln Glu Ser Ile Trp Ala Asn Gln Ile Leu Asp Lys Ala Gln Leu Val (SEQ ID NO:11), which matches perfectly with the N-terminal amino acid sequence derived by amino acid sequencing of the native protein.

To clone the rest of the endonuclease gene, a set of inverse PCR primers was designed from the 59 bp DNA sequence.

The inverse PCR primers are as follows:

5' GATATTGGACAAGGCCCAACTGGT 3'  (SEQ ID NO:12)
5' TATTGATTCTTGGTTTTCTCCCAT 3'  (SEQ ID NO:13)

*B. stearothermophilus* H3 genomic DNA was digested with the following restriction enzymes with 6 bp recognition sequences AatII, BamHI, BgiII, BspEI, ClaI, EcoRI, HindIII, MluI, NheI, or SphI, and restriction enzymes with 4–5 bp recognition sequences, Sau3AI, NlaIII, MspI, MboI, HinPII, HhaI, HpaIII HaeII, EaeI, or AciI for two hours at the required temperatures. The digestions gave rise to reasonable size template DNA (less than 10 kb) for inverse PCR reaction. The digested DNA samples were self-ligated at a low DNA concentration (less than 2 microgram per ml). The ligated circular DNA was extracted twice with phenol-CHCl₃ and once with CHCl₃. The DNA was precipitated with ethanol, resuspended in TE beffer, and used as templates for inverse PCR reactions (95° C. 1 min, 60° C. 1 min, 72° C. 2 min, 30 cycles). PCR products were found in Sau3AI, MboI, and AciI digested and self-ligated genomic DNA. The DNA fragments were cloned into pUC19 and sequenced, which gave rise to 465 bp of new sequence.

To clone the rest of the endonuclease gene, a second set of inverse PCR primers were designed from the end of 465 bp new sequence. The primer sequences are as follows:

5' TCCGCTAATTACCTTACCATTATTGGT 3'  (SEQ ID NO:14)
5' CTTTAACTTCAGCCAATAGCATTATGT 3'  (SEQ ID NO:15)

Two primers were used to amplify additional surrounding DNA. *B. stearothermophilus* H3 genomic DNA was digested with ApoI, BsaWI, Sau3AI, NlaII, MspI, MboI, HinPII, HhaI, HpaII, HaeII, EaeI, TaiI, HinfI, RsaI, or AciI. The digested DNA samples were self-ligated at a low DNA concentration (less than 2 microgram per ml). The ligated circular DNA was extracted twice with phenol-CHCl₃ and once with CHCl₃. The DNA was precipitated with ethanol and resuspended in TE buffer. The ligated circular DNA was used as templates for inverse PCR reaction (95° C. 1 min, 60° C. 1 min, 72° C. 2 min, 30 cycles). Inverse PCR products were found in HinfI or RsaI digested and self-ligated genomic DNA. The DNA fragments were cloned and sequenced. After 730 bp of additional sequence, a stop codon was found in the sequenced RsaI fragment. The entire BssHII endonuclease gene shown in FIG. 2 is 1254 bp (59 bp+465 bp+730 bp), encoding the 417-aa BssHII endonuclease with predicted molecular mass of 47 kDa, which matches closely with the apparent size (46.5 kDa) on an SDS-PAGE gel.

3. Expression of bssHIIR gene in pUC19

To premodify *E. coli* host, the multi-specific BssHII methylase gene was cloned into pACYC184. The entire BssHII endonuclease gene was amplified by PCR with two primers. An efficient ribosome binding site and 7 bp spacing were engineered before the ATG start codon. The endonuclease gene was cloned into pUC19. Three clones with inserts were found, but no apparent BssHII activity was found in cell extract of IPTG-induced cell cultures. It was concluded that the inserts may carry mutations during PCR amplifications. Expression of BssHII endonuclease gene from pUC19 may also be unstable due to leaky expression.

4. Expression of bssHIIR gene in the T7 expression vector pET21AT.

In a second attempt to express the bssHIIR gene, a T7 expression vector pET21AT was used for tightly-regulated expression. Vector pET21AT carries four copies of transcription terminators upstream of the T7 promoter. The co-transformation of pLysS further reduces the basal level expression under non-induced condition. The bssHIIM1 gene was amplified by PCR and cloned into a compatible vector pLG339 (derived from pSC101). Two primers were designed for bssHIIR gene amplification are as follows:

forward primer:

(XbaI site)
5' AGCTCTAGAGGAGGTAAATAAATGGGAGAAAACCAAGAATCA ATATGGGCA 3' (SEQ ID NO:16)

reverse primer:

(BamHI site)
5' CGCGGATCCTCAGAATTGGAAGTTTTCTCTAATCCATTCATC 3' (SEQ ID NO:17)

The bssHIIR gene was amplified by PCR using Vent® polymerase (95° C. 1 min, 60° C. 1 min, 72° C. 1 min, 20 cycles) and cloned into pET21AT. *E. coli* host cell for T7 expression, ER2504, was transformed with pLysS, pLG-BssHIIM1, pET21AT-BssHIIR. Twelve isolates were cultured to late log growth phase (about 120 klett units). IPTG was added to a final concentration of 0.5 mM. IPTG induction was carried out for three hours and cell extracts were prepared and assayed for BssHII restriction endonuclease activity. All 12 clones produced BssHII endonuclease. One clone was induced in 500 ml cell culture and its cell extract was diluted 10-, 100-, 1000-fold and used to assay BssHII endonuclease activity on lambda DNA. FIG. 5 shows the assay result. The cell extract displayed BssHII activity after 10- and 100-fold dilutions (lanes 2 and 3).

5. Cloning of bssHIIM2 gene.

In type II restriction-modification systems, the restriction endonuclease gene and its cognate methylase gene are usually arranged in close proximity to each other. The DNA upstream of the bssHIIR gene was amplified by inverse PCR, cloned, and sequenced. The upstream sequence has homolgy to known ribosomal rRNA sequence. Therefore, it was reasoned that the true BssHII methylase gene (bssHIIM2) must be located downstream of the restriction endonuclease gene. To clone the methylase gene downstream of the bssHIIR gene, a set of primers were made as follows:

5' TCTTTCGTCGCTCAGGTTCTGAAGTAC 3'  (SEQ ID NO:18)
5' TGATTAAAAACAAAGTCGAAAGATTCG 3'  (SEQ ID NO:19)

*B. stearothermophilus* H3 genomic DNA was digested with AciI, AluI, ApoI, BsaWI, EaeI, HhaI, HaeII, HaeIII, MseI, Sau3AI, or Tsp509I. The digested DNA samples were self-ligated at a low DNA concentration (less than 2 microgram per ml). The ligated circular DNA was extracted twice with phenol-CHCl₃ and once with CHCl₃. The DNA was precipitated with ethanol and resuspended in TE buffer. The ligated circular DNA was used as templates for inverse PCR reaction (95° C. 1 min, 55° C. 1 min, 72° C. 2 min, 30 cycles). Inverse PCR products were found in the inverse PCR reactions of HhaI, HaeIII, and Sau3AL digested and self-ligated genomic DNA. The three inverse PCR products were cloned and sequenced. An unfinished open reading frame was found in the newly derived 895 bp sequence and it was compared to the known genes in Genbank. This unfinished open reading frame has amino acid sequence similarity to the known $C^5$ methylases.

To clone the rest of the bssHIIM2 gene, a second set of inverse PCR primers were synthesized as follows:

5' GGAAAATGTAGCGAACTTGAAAGGTGT 3'  (SEQ ID NO:20)
5' ACAAAGAATGGAGGGTTGATTTTCTCA 3'  (SEQ ID NO:21)

These two primers were used to amplify the downstream sequences. *B. stearothermophilus* H3 genomic DNA was digested with AvaI, AluI, BsaJI, BstNI, Csp6I, DpnII, EcoO109I, HaeIII, HinfII, MboI, MseI, RsaI, Sau3AI, Sau96I, SpeI, StyI, TaiI, TfiI, Tsp45I, or Tsp509I. The digested DNA samples were self-ligated at a low DNA concentration (less than 2 microgram per ml). The ligated circular DNA was extracted twice with phenol-CHCl$_3$ and once with CHCl$_3$. The DNA was precipitated with ethanol and resuspended in TE buffer. The ligated circular DNA was used as templates for inverse PCR reaction (95° C. 1 min, 55° C. 1 min, 72° C. 2 min, 30 cycles). Inverse PCR products were found in the inverse PCR reactions of HaeIII, HinfII, MboI, Sau3AI, and StyI digested and self-ligated genomic DNA. Inverse PCR product from StyI digested and self-ligated DNA was cloned into pUC19 and the insert was sequenced. A stop codon was found in the newly derived 250 bp DNA sequence. The entire BssHII methylase gene (bssHIIM2), shown in FIG. 4, is 1128 bp, encoding the 375-aa BssHII methylase protein with molecular mass of 42.2 kDa.

6. Expression of bssHIIR gene in bssHIIM2 premodified host cell.

The entire bssHIIM2 gene was amplified using two primers:

5' CAAGGATCC (BamHI site) GGAGGT (ribosome binding site) TAATTAAATGAATGGATTAGAGAAAACTTCCAAT 3'
(SEQ ID NO:22)

5' TTCGGATCC (BamHI site) TTAAACAAGTTTAGGTAAACCTTT GAAGGC 3'  (SEQ ID NO:23)

The bssHIIM2 gene was inserted into plasmid vector pLG339.

The pre-modified *E. coli* host cell ER2417 [pLysP, pLG-BssHIIM2] was transformed with pET21AT-BssHIIR. The resulting strain ER2417 [pLysP, pLG-BssHIIM2, pET21AT-25 BssHIIR] was cultured at 30° C. in 500 ml LB plus Ap (50 µg/ml), Km (50 µg/ml), Cm (30 µg/ml) to late log phase (120–150 klett units). IPTG was added to the culture to a final concentration of 0.5 mM. Following IPTG induction for three hours, cells were harvested and lysed with lysozyme and sonications. The cell extract was assayed for BssHII activity on lambda DNA. The clone produced 1×10$^5$ units of BssHII restriction endonuclease per gram of wet *E. coli* cells.

---

What is claimed is:

1. Isolated DNA coding for the BssHII restriction endonuclease, wherein the isolated DNA is obtainable from *B. stearothermophilus*.

2. A recombinant DNA vector comprising a vector into which a DNA segment coding for the BssHII restriction endonuclease has been inserted.

3. Isolated DNA coding for the BssHII restriction endonuclease and methylase, wherein the isolated DNA is obtainable from ATCC No. 98334.

4. A cloning vector which comprises the isolated DNA of claim 3.

5. A host cell transformed by the vector of claims 2 or 4.

6. A method of producing a BssHII restriction endonuclease comprising culturing a host cell transformed with the vector of claims 2 or 4 under conditions suitable for expression of said endonuclease.

* * * * *

UNITED STATES PATENT AND TRADEMARK OFFICE
CERTIFICATE OF CORRECTION

PATENT NO. : 5,786,195

DATED : July 28, 1998

INVENTOR(S) : Xu, et al.

It is certified that error appears in the above-identified patent and that said Letters Patent is hereby corrected as shown below:

Cover page, Section [57], Abstract, replace "MIuI" with --MluI--

Column 3, line 24, replace "(Met) Gly Glu Asn Gln Glu" with --(Met) Gly Glu Asn Gln Glu--

Column 3, line 25, replace "Asp Lys Ala Gln Leu Val" with --Asp Ly Ala Gln Leu Val--

Column 4, line 18, replace "BssH11M1" with --BssHII1--

Column 4, line 34, replace "BssH11M2" with --BssHIIM2--

Column 4, line 36, replace "BssH11M2" with --BssHIIM2--

Column 5, line 50, replace "5°" with --5'--

Column 5, line 45-46, replace "(Met) Gly Glu Asn Gln Glu" with --(Met) Gly Glu Asn Gln Glu--

Column 5, line 46-47, replace "Asp Lys Ala Gln Leu Val" with --Asp Lys Ala gln Leu Val--

Column 6, line 13, replace "NlaI1" with --NlaIII--

UNITED STATES PATENT AND TRADEMARK OFFICE
CERTIFICATE OF CORRECTION

PATENT NO. : 5,786,195

DATED : July 28, 1998

INVENTOR(S) : Xu, et al.

It is certified that error appears in the above-identified patent and that said Letters Patent is hereby corrected as shown below:

```
Column 6, line 50, replace "Moffaft" with --Moffatt"

Column 6, line 50, replace "J. MoL." with -- J. Mol.--

Column 6, line 60, replace "BssH11M1" with --BssHIIM1--

Column 7, line 9, replace "Styl" with --StyI--

Column 7, line 17, replace "BssH11M2" with --BssHIIM2--

Column 7, line 19, replace "BssH11M2" with --BssHIIM2--

Column 7, line 24, replace "CoIlection" with
     --Collection--

Column 7, line 43, replace "Sau3AL" with --Sau3AI--

Column 7, line 44, replace "Sau3AL" with --Sau3AI--

Column 7, line 59, replace "BssH11" with --BssHII--

Column 8, line 17, replace "(Met) Gly Glu Asn Gln Glu"
     with --(Met) Gly Glu Asn Gln Glu--

Column 8, line 18, replace "Asp Lys Ala Gln Leu Val"
     with --Asp Lys Ala Gln Leu Val--

Column 8, line 22, replace "(Met) Gly Glu Asn Gln Glu"
     with --(Met) Gly Glu Asn Gln Glu--

Column 8, line 30, replace "Asp Lys Ala Gln Leu Val"
     with --Asp Lys Ala Gln Leu Val--
```

UNITED STATES PATENT AND TRADEMARK OFFICE
CERTIFICATE OF CORRECTION

PATENT NO. : 5,786,195

DATED : July 28, 1998

INVENTOR(S) : Xu, et al.

It is certified that error appears in the above-identified patent and that said Letters Patent is hereby corrected as shown below:

Column 8, line 61-62, replace "(Met) Gly Glu Asn Gln Glu" with --(Met) Gly Glu Asn Gln Glu--

Column 8, line 62-63, replace "Asp Lys Ala Gln Leu Val" with --Asp Lys Ala Gln Leu Val--

Column 9, line 8, replace "BgiII" with --BglII--

Column 9, line 11, replace "HpaI11" with --HpaII--

Column 9, line 16, replace CHCI$_3$" with --CHCl$_3$--

Column 9, line 16, replace CHCI$_3$" with --CHCl$_3$--

Column 9, line 32, replace "Apo1" with --ApoI--

Column 9, line 32, replace "Nla11" with --NlaIII--

Column 9, line 36, replace "CHCI$_3$" with --CHCl$_3$--

Column 9, line 37, replace CHCI$_3$" with --CHCl$_3$--

Column 10, line 21, replace "BssH11M1" with --BssHIIM1--

Column 10, line 50, replace "Alu1, Apo1, BsaW1" with --AluI, ApoI, BsaWI--

Column 10, line 59, replace "Sau3AL" with --Sau3AI--

UNITED STATES PATENT AND TRADEMARK OFFICE
CERTIFICATE OF CORRECTION

PATENT NO. : 5,786,195
DATED : July 28, 1998
INVENTOR(S) : Xu, et al.

It is certified that error appears in the above-identified patent and that said Letters Patent is hereby corrected as shown below:

Column 10, line 4, delete "were"

Column 10, line 38, replace "homolgy" with --homology--

Column 35, claim 1, last line, replace
  "B. stearothermophilus" with
  --B. stearothermophilus H3--

Column 11, line 11, replace "CHCI$_3$" with --CHCl$_3$--

Column 11, line 12, replace CHCI$_3$" with --CHCl$_3$--

Column 11, line 17, replace "Sty1" with --StyI--

Column 11, line 18, replace "Sty1" with --StyI--

Column 12, line 15, replace "BssH11M2" with --BssHIIM2--

Column 12, line 16, replace "BssH11M2" with --BssHIIM2--

Column 12, line 17, replace "25 BssHIIR" with --BssHIIR--

Signed and Sealed this

Fifteenth Day of December, 1998

*Attest:*

BRUCE LEHMAN

*Attesting Officer*     Commissioner of Patents and Trademarks

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:1:

Met Gly Glu Asn Gln Glu Ser Ile Trp Ala Asn Gln Ile Leu Asp Lys
1               5                   10                  15

Ala Gln Leu Val Ser Pro Glu Thr His Xaa Gln Asn Xaa Ala Asp
            20                  25                  30

( 2 ) INFORMATION FOR SEQ ID NO:2:

( i ) SEQUENCE CHARACTERISTICS:
        ( A ) LENGTH: 1608 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO -continued (iv) ANTI-SENSE: NO (v) FRAGMENT TYPE:

(vi) ORIGINAL SOURCE:

(ix) FEATURE:
    (A) NAME/KEY: Coding Sequence
    (B) LOCATION: 1...1605
    (D) OTHER INFORMATION:

(xi) SEQUENCE DESCRIPTION: SEQ ID NO:2:

```
ATG ACG TTC GAC GTA ACG CCA CAA TTA CCG GAC AGC GGC CTG ACC GTC        48
Met Thr Phe Asp Val Thr Pro Gln Leu Pro Asp Ser Gly Leu Thr Val
 1               5                  10                  15

GCG GAA CTA TTC GCA GGG GGC GGT CTA ATG GCG GTC GGC CTC CGC GCT        96
Ala Glu Leu Phe Ala Gly Gly Gly Leu Met Ala Val Gly Leu Arg Ala
                20                  25                  30

GCC GGT TAC AAT CTC GTA TGG GCC AAC GAC TTC GAT AAG TCG GCT TGC       144
Ala Gly Tyr Asn Leu Val Trp Ala Asn Asp Phe Asp Lys Ser Ala Cys
        35                  40                  45

GCC GCC TAC CGC CAT AAT CTC GGC GAC CAC ATC GTA CAC GGC GAC ATT       192
Ala Ala Tyr Arg His Asn Leu Gly Asp His Ile Val His Gly Asp Ile
50                  55                  60

ACC GCG ATT GAT CCC GCT GAC ATT CCG GAC ACC GAC GTG ATT GCC GGT       240
Thr Ala Ile Asp Pro Ala Asp Ile Pro Asp Thr Asp Val Ile Ala Gly
65                  70                  75                  80

GGC CCG CCT TGT CAG GAT TAC AGC GTC GCG GGA ACC GGT GCG GGC GAA       288
Gly Pro Pro Cys Gln Asp Tyr Ser Val Ala Gly Thr Gly Ala Gly Glu
                85                  90                  95

GAG GGC GAA CGC GGC AAG CTC GTG TGG GCG TAC CTG CGG ATT ATC GAG       336
Glu Gly Glu Arg Gly Lys Leu Val Trp Ala Tyr Leu Arg Ile Ile Glu
                100                 105                 110

GCG AAG CGT CCG AAA GCG TTC ATA TTC GAG AAC GTG AAG GGT CTC ATT       384
Ala Lys Arg Pro Lys Ala Phe Ile Phe Glu Asn Val Lys Gly Leu Ile
        115                 120                 125

ACG AAA AAG CAC CGC CCG ACA TTC GAT GCG TTG CTG AAA CAA TTT AAG       432
Thr Lys Lys His Arg Pro Thr Phe Asp Ala Leu Leu Lys Gln Phe Lys
130                 135                 140

ATA ATC GGG TAT AAC GTG TCA TGG AAA CTC ATC AAC GCA TGG GAC TAC       480
Ile Ile Gly Tyr Asn Val Ser Trp Lys Leu Ile Asn Ala Trp Asp Tyr
145                 150                 155                 160

GGA GTG GCG CAG AAG AGG GAG CGT GTG TTC ATC GTG GGC ATC CGC GCT       528
Gly Val Ala Gln Lys Arg Glu Arg Val Phe Ile Val Gly Ile Arg Ala
                165                 170                 175

GAT CTA GGA TTT GCG TTT GAG TTT CCG GAA CCG CGA CCG GGG GAC TAC       576
Asp Leu Gly Phe Ala Phe Glu Phe Pro Glu Pro Arg Pro Gly Asp Tyr
                180                 185                 190

CGG ACG CAA GTG CTG CGC GAT GTG ATC GGG GAT TTG CCG GAG CCG GTC       624
Arg Thr Gln Val Leu Arg Asp Val Ile Gly Asp Leu Pro Glu Pro Val
        195                 200                 205

GAT ACT TGC GGC CGA CGC GTG AAG AAG GTG GAA CGT GTC GCG GAC ATG       672
Asp Thr Cys Gly Arg Arg Val Lys Lys Val Glu Arg Val Ala Asp Met
210                 215                 220

AAC GAG CCG GGG CCG ACG GTG ACG ACA CAG TTC CGT TGT CAG ACG GTC       720
Asn Glu Pro Gly Pro Thr Val Thr Thr Gln Phe Arg Cys Gln Thr Val
225                 230                 235                 240

GAG ATT ACG AAT CAC AAC GGG GGA GTC CCG GCG AAA GAA TAT CCC GGT       768
Glu Ile Thr Asn His Asn Gly Gly Val Pro Ala Lys Glu Tyr Pro Gly
                245                 250                 255

CAC ACT GCG TCG AGT CTC GAA GGA CCA GCG AAG AAA ACG ATT GTG GCG       816
His Thr Ala Ser Ser Leu Glu Gly Pro Ala Lys Lys Thr Ile Val Ala
                260                 265                 270
```

```
GGC GCA AAC GGC GTG CCC GGC GGC GCG AAT TGT TTC TAT CCG AAC CAC      864
Gly Ala Asn Gly Val Pro Gly Gly Ala Asn Cys Phe Tyr Pro Asn His
    275             280                 285

GAA CGC AAA GAA ATC AGC GAA AAG GCG CTC GCA GGC TAC GAA CGG CGC      912
Glu Arg Lys Glu Ile Ser Glu Lys Ala Leu Ala Gly Tyr Glu Arg Arg
    290             295                 300

GGA GGA CAG GGT GGA TTT GGA TTC CGC GTG AAC CAA TGG GAC GAT CCG      960
Gly Gly Gln Gly Gly Phe Gly Phe Arg Val Asn Gln Trp Asp Asp Pro
305             310                 315                 320

TCG CCT ACG ATA TTC GGC CGG ATT TTT AAC GAA GGA AAG GCG TTC GT      1008
Ser Pro Thr Ile Phe Gly Arg Ile Phe Asn Glu Gly Lys Ala Phe Val
                325                 330                 335

CAT CCG GGG CCT ATC GAA AAT CAC GAT GAA AAA TCG TTC TGG ACG CC      1056
His Pro Gly Pro Ile Glu Asn His Asp Glu Lys Ser Phe Trp Thr Pro
        340                 345                 350

AAA TCC GAA TAC ACC TAC GAC CAA GCT AAT CGT GTA CAG TCG TGG GA      1104
Lys Ser Glu Tyr Thr Tyr Asp Gln Ala Asn Arg Val Gln Ser Trp Asp
        355                 360                 365

AAG CCA AGT GCC ACA ATC CCC GCG CAT CAC AAC AGT GGA CAG CCG AA      1152
Lys Pro Ser Ala Thr Ile Pro Ala His His Asn Ser Gly Gln Pro Asn
    370                 375                 380

CAT CCG CAG TAC GCG AAC CAC GAC CGG TAC GCT GTC CTC GCG AAG GA      1200
His Pro Gln Tyr Ala Asn His Asp Arg Tyr Ala Val Leu Ala Lys Asp
385             390                 395                 400

AGC GAC GTG ATT CCG AAA ATC CCC GAA GGA GCG TCG AAT CGA CAA GC      1248
Ser Asp Val Ile Pro Lys Ile Pro Glu Gly Ala Ser Asn Arg Gln Ala
                405                 410                 415

GCA AAG ATA GAA CCG GAC ATT TAT TGG TCG GAC TAT ATC CGG GAG AG      1296
Ala Lys Ile Glu Pro Asp Ile Tyr Trp Ser Asp Tyr Ile Arg Glu Ser
        420                 425                 430

CGC GAA AAC CCT GCA CGC ACA ATG ATC GGT ACA GGT AAG CCG AAG AT      1344
Arg Glu Asn Pro Ala Arg Thr Met Ile Gly Thr Gly Lys Pro Lys Ile
        435                 440                 445

CAC CCG ACA CAG CCC CGC CGT TTC ACT GTC CGC GAG TGC CTG CGG AT      1392
His Pro Thr Gln Pro Arg Arg Phe Thr Val Arg Glu Cys Leu Arg Ile
    450                 455                 460

CAA TCG GTG CCC GAC TGG TAC GTG CTG CCG GAT GAC ATT TCG CTA TC      1440
Gln Ser Val Pro Asp Trp Tyr Val Leu Pro Asp Asp Ile Ser Leu Ser
465             470                 475                 480

GCG CAA TAC CGT ATC GTC GGC AAC GGG ATA GCG TCG CGC GTC GCG TA      1488
Ala Gln Tyr Arg Ile Val Gly Asn Gly Ile Ala Ser Arg Val Ala Tyr
                485                 490                 495

TTG CTC GGA ATT GCC CTG GCG GAA CAA CTC CGT GCC GCA ACG GAA TC      1536
Leu Leu Gly Ile Ala Leu Ala Glu Gln Leu Arg Ala Ala Thr Glu Ser
        500                 505                 510

AGC GCA ATA GGC GAG CGT TTG ATT GCG GAT AAT ACG GAC GAC TGC GC      1584
Ser Ala Ile Gly Glu Arg Leu Ile Ala Asp Asn Thr Asp Asp Cys Ala
        515                 520                 525

AAC AGT CGG AAG GAG GCG GTC TAG                                      1608
Asn Ser Arg Lys Glu Ala Val
530                 535
```

( 2 ) INFORMATION FOR SEQ ID NO:3:

( i ) SEQUENCE CHARACTERISTICS:
        ( A ) LENGTH: 1254 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
  ( A ) NAME/KEY: Coding Sequence
  ( B ) LOCATION: 1...1251
  ( D ) OTHER INFORMATION:

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GGA | GAA | AAC | CAA | GAA | TCA | ATA | TGG | GCA | AAT | CAG | ATA | TTG | GAC | AAG | 48 |
| Met | Gly | Glu | Asn | Gln | Glu | Ser | Ile | Trp | Ala | Asn | Gln | Ile | Leu | Asp | Lys | |
| 1 | | | | 5 | | | | | 10 | | | | | 15 | | |
| GCC | CAA | CTG | GTT | ATG | CCA | GAA | ACT | CAT | GAA | CAA | AAT | TTA | GCT | GAT | ACT | 96 |
| Ala | Gln | Leu | Val | Met | Pro | Glu | Thr | His | Glu | Gln | Asn | Leu | Ala | Asp | Thr | |
| | | | 20 | | | | | 25 | | | | | 30 | | | |
| TTG | ATT | GAC | TTA | TGT | TAC | AAT | GCA | GCA | AAG | AGA | ACT | AAT | GTT | CCC | GTC | 144 |
| Leu | Ile | Asp | Leu | Cys | Tyr | Asn | Ala | Ala | Lys | Arg | Thr | Asn | Val | Pro | Val | |
| | | 35 | | | | | 40 | | | | | 45 | | | | |
| GGA | ATT | GCT | CTG | GCT | GCA | TCA | TTC | GAT | TTA | TTG | GTA | GGA | GCC | GAG | TAT | 192 |
| Gly | Ile | Ala | Leu | Ala | Ala | Ser | Phe | Asp | Leu | Leu | Val | Gly | Ala | Glu | Tyr | |
| | | 50 | | | | | 55 | | | | | 60 | | | | |
| TAT | AGA | AAC | GTA | ATC | AAC | AGA | GGG | TGG | TGT | TAC | TGT | CCA | GAA | CAC | CAA | 240 |
| Tyr | Arg | Asn | Val | Ile | Asn | Arg | Gly | Trp | Cys | Tyr | Cys | Pro | Glu | His | Gln | |
| 65 | | | | | 70 | | | | | 75 | | | | | 80 | |
| TCT | TTA | ATT | TTC | CCT | TAT | ACA | AAT | ACT | TGC | CCT | GCA | TGT | GTA | CTT | TCG | 288 |
| Ser | Leu | Ile | Phe | Pro | Tyr | Thr | Asn | Thr | Cys | Pro | Ala | Cys | Val | Leu | Ser | |
| | | | | 85 | | | | | 90 | | | | | 95 | | |
| GGA | AAA | TTT | CAT | TTT | CAT | CGT | TCT | AAT | AAA | CCG | GAA | TCG | GGG | AAA | ATC | 336 |
| Gly | Lys | Phe | His | Phe | His | Arg | Ser | Asn | Lys | Pro | Glu | Ser | Gly | Lys | Ile | |
| | | | 100 | | | | | 105 | | | | | 110 | | | |
| GGT | ACG | GCA | ACT | TCC | CGC | TTG | CTT | TGC | GTA | TTT | CTG | GAC | AGG | CTT | TTT | 384 |
| Gly | Thr | Ala | Thr | Ser | Arg | Leu | Leu | Cys | Val | Phe | Leu | Asp | Arg | Leu | Phe | |
| | | 115 | | | | | 120 | | | | | 125 | | | | |
| GTA | AAA | TCA | TCA | AGG | AAC | TTT | AAG | ATT | TTC | AAA | GGC | AGT | GAA | CCT | ATT | 432 |
| Val | Lys | Ser | Ser | Arg | Asn | Phe | Lys | Ile | Phe | Lys | Gly | Ser | Glu | Pro | Ile | |
| | 130 | | | | | 135 | | | | | 140 | | | | | |
| GAT | ATT | TTA | ATA | CAC | GAT | GAG | CAG | AAA | AAC | ATA | ATG | CTA | TTG | GCT | GAA | 480 |
| Asp | Ile | Leu | Ile | His | Asp | Glu | Gln | Lys | Asn | Ile | Met | Leu | Leu | Ala | Glu | |
| 145 | | | | | 150 | | | | | 155 | | | | | 160 | |
| GTT | AAA | GCT | GCT | CCG | CTA | ATT | ACC | TTA | CCA | TTA | TTG | GTT | CGA | TCT | GAA | 528 |
| Val | Lys | Ala | Ala | Pro | Leu | Ile | Thr | Leu | Pro | Leu | Leu | Val | Arg | Ser | Glu | |
| | | | | 165 | | | | | 170 | | | | | 175 | | |
| GAA | AAA | ATT | ACC | GAT | TTA | GTC | GAT | GGT | GAA | ATA | GTT | GAA | ATA | CCA | CAT | 576 |
| Glu | Lys | Ile | Thr | Asp | Leu | Val | Asp | Gly | Glu | Ile | Val | Glu | Ile | Pro | His | |
| | | | 180 | | | | | 185 | | | | | 190 | | | |
| TCT | GCC | GTA | GAC | AAC | TCA | TCT | TTA | TCT | TCA | TCA | AAT | ATT | TGC | TTG | CTT | 624 |
| Ser | Ala | Val | Asp | Asn | Ser | Ser | Leu | Ser | Ser | Ser | Asn | Ile | Cys | Leu | Leu | |
| | | 195 | | | | | 200 | | | | | 205 | | | | |
| CTC | CCT | GTT | TTT | CAT | GAT | GGG | AGT | TGG | CAA | AGT | AAA | TTT | GTT | GAA | CTT | 672 |
| Leu | Pro | Val | Phe | His | Asp | Gly | Ser | Trp | Gln | Ser | Lys | Phe | Val | Glu | Leu | |
| | 210 | | | | | 215 | | | | | 220 | | | | | |
| CAA | ACG | AAA | GAT | GAT | ATA | TTA | ACA | AAT | ACC | ATT | TGG | GCA | TAC | GGC | CAG | 720 |
| Gln | Thr | Lys | Asp | Asp | Ile | Leu | Thr | Asn | Thr | Ile | Trp | Ala | Tyr | Gly | Gln | |
| 225 | | | | | 230 | | | | | 235 | | | | | 240 | |
| CTA | GAA | AAT | ATT | TTT | AGG | GGA | AAT | AAT | GAT | CTT | TTT | GAT | TTA | TAC | TTA | 768 |
| Leu | Glu | Asn | Ile | Phe | Arg | Gly | Asn | Asn | Asp | Leu | Phe | Asp | Leu | Tyr | Leu | |
| | | | | 245 | | | | | 250 | | | | | 255 | | |
| GAT | ACT | TGG | AAA | AGG | GCA | TTC | GAA | GCA | TAT | CAG | GTG | GCT | TAT | CAC | GAA | 816 |

|  |  |  |  |  |  |  |  |  |  |  |  |  |  |  |  |
|---|---|---|---|---|---|---|---|---|---|---|---|---|---|---|---|
| Asp | Thr | Trp | Lys<br>260 | Arg | Ala | Phe | Glu<br>265 | Ala | Tyr | Gln | Val | Ala<br>270 | Tyr | His | Glu |

| AAA | GAT | AGA | TCA | AGC | AAC | ATT | TTT | TGG | TTG | ACA | AAT | GCT | TGT | GGA | CAA | 864 |
|---|---|---|---|---|---|---|---|---|---|---|---|---|---|---|---|---|
| Lys | Asp | Arg<br>275 | Ser | Ser | Asn | Ile | Phe<br>280 | Trp | Leu | Thr | Asn | Ala<br>285 | Cys | Gly | Gln | |

| CCT | GAG | CCA | AGA | CCT | GTC | GAT | TGG | CCC | GCT | AGA | TCG | GGA | ACA | GGT | TAT | 912 |
|---|---|---|---|---|---|---|---|---|---|---|---|---|---|---|---|---|
| Pro | Glu<br>290 | Pro | Arg | Pro | Val | Asp<br>295 | Trp | Pro | Ala | Arg | Ser<br>300 | Gly | Thr | Gly | Tyr | |

| GAA | TCT | GTT | TCT | GAT | GGA | AAA | ACT | AGT | GTG | GGC | ATG | GAT | AGA | ACT | GAC | 960 |
|---|---|---|---|---|---|---|---|---|---|---|---|---|---|---|---|---|
| Glu<br>305 | Ser | Val | Ser | Asp | Gly<br>310 | Lys | Thr | Ser | Val | Gly<br>315 | Met | Asp | Arg | Thr | Asp<br>320 | |

| GAT | ATT | AAA | AAA | GGA | ATT | TAT | CAA | GTG | TTA | AAG | CTG | GGC | GCT | GAG | AG1 | 008 |
|---|---|---|---|---|---|---|---|---|---|---|---|---|---|---|---|---|
| Asp | Ile | Lys | Lys | Gly<br>325 | Ile | Tyr | Gln | Val | Leu<br>330 | Lys | Leu | Gly | Ala | Glu<br>335 | Ser | |

| AAG | CCC | ATA | AAC | CAG | CAG | TAT | CAA | ATT | AAA | ACA | GCA | CTA | ATA | TCA | AA1 | 056 |
|---|---|---|---|---|---|---|---|---|---|---|---|---|---|---|---|---|
| Lys | Pro | Ile | Asn<br>340 | Gln | Gln | Tyr | Gln | Ile<br>345 | Lys | Thr | Ala | Leu | Ile<br>350 | Ser | Asn | |

| ATT | CAT | GCC | GCG | AGA | CAC | TAC | GAC | GAA | TAT | CTA | ACC | TCA | TTG | CAA | GA1 | 104 |
|---|---|---|---|---|---|---|---|---|---|---|---|---|---|---|---|---|
| Ile | His | Ala<br>355 | Ala | Arg | His | Tyr | Asp<br>360 | Glu | Tyr | Leu | Thr | Ser<br>365 | Leu | Gln | Asp | |

| GTA | GTT | TGG | GCA | TTA | GAT | GAA | ACA | GGA | TTA | GCT | AAG | AAA | GCA | GGT | GA1 | 152 |
|---|---|---|---|---|---|---|---|---|---|---|---|---|---|---|---|---|
| Val | Val | Trp<br>370 | Ala | Leu | Asp | Glu | Thr<br>375 | Gly | Leu | Ala | Lys | Lys<br>380 | Ala | Gly | Glu | |

| CTT | GAC | AGT | GAG | ACA | CCA | ATC | TAC | AAC | TTA | TTT | GAC | GGA | ATC | ATT | TC1 | 200 |
|---|---|---|---|---|---|---|---|---|---|---|---|---|---|---|---|---|
| Leu | Asp | Ser | Glu | Thr<br>390 | Pro | Ile | Tyr | Asn | Leu<br>395 | Phe | Asp | Gly | Ile | Ile<br>400 | Ser | |
| 385 | | | | | | | | | | | | | | | | |

| TTT | ACG | CGA | AAT | CAC | CCT | AGA | GAT | GAA | TGG | ATT | AGA | GAA | AAC | TTC | CA1 | 248 |
|---|---|---|---|---|---|---|---|---|---|---|---|---|---|---|---|---|
| Phe | Thr | Arg | Asn | His<br>405 | Pro | Arg | Asp | Glu | Trp<br>410 | Ile | Arg | Glu | Asn | Phe<br>415 | Gln | |

| TTC | TGA | | | | | | | | | | | | | | | 1254 |
|---|---|---|---|---|---|---|---|---|---|---|---|---|---|---|---|---|
| Phe | | | | | | | | | | | | | | | | |

( 2 ) INFORMATION FOR SEQ ID NO:4:

( i ) SEQUENCE CHARACTERISTICS:
           ( A ) LENGTH: 1128 base pairs
           ( B ) TYPE: nucleic acid
           ( C ) STRANDEDNESS: single
           ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
           ( A ) NAME/KEY: Coding Sequence
           ( B ) LOCATION: 1...1125
           ( D ) OTHER INFORMATION:

( x i ) SEQUENCE DESCRIPTION: SEQ ID NO:4:

| ATG | AAT | GGA | TTA | GAG | AAA | ACT | TCC | AAT | TCT | GAC | GAA | TCT | TTC | GAC | TTT | 48 |
|---|---|---|---|---|---|---|---|---|---|---|---|---|---|---|---|---|
| Met<br>1 | Asn | Gly | Leu | Glu<br>5 | Lys | Thr | Ser | Asn | Ser<br>10 | Asp | Glu | Ser | Phe | Asp<br>15 | Phe | |

| GTT | TTT | AAT | CAT | GTC | TTT | CGT | CGC | TCA | GGT | TCT | GAA | GTA | CAA | AAA | AGA | 96 |
|---|---|---|---|---|---|---|---|---|---|---|---|---|---|---|---|---|
| Val | Phe | Asn | His<br>20 | Val | Phe | Arg | Arg | Ser<br>25 | Gly | Ser | Glu | Val | Gln<br>30 | Lys | Arg | |

| ATT | GAT | GCA | CTA | AAA | ATC | GGT | CAA | AAA | ATG | CAA | GAC | CTG | CCT | GAA | GAA | 144 |
|---|---|---|---|---|---|---|---|---|---|---|---|---|---|---|---|---|
| Ile | Asp | Ala<br>35 | Leu | Lys | Ile | Gly | Gln<br>40 | Lys | Met | Gln | Asp | Leu<br>45 | Pro | Glu | Glu | |

-continued

| | | | | | | | | | | | | | | | | |
|---|---|---|---|---|---|---|---|---|---|---|---|---|---|---|---|---|
| CTA | TGG | CAT | GAC | AGC | TTT | CGT | TAT | TAT | GTA | AAG | GAA | GAC | CCA | AAT | AGA | 192 |
| Leu | Trp | His | Asp | Ser | Phe | Arg | Tyr | Tyr | Val | Lys | Glu | Asp | Pro | Asn | Arg | |
| | 50 | | | | 55 | | | | | 60 | | | | | | |
| CGC | GGC | GGC | CCA | AAC | ATG | CGA | ATG | ATA | CGC | CTT | GAT | CCG | TCT | AAA | CCT | 240 |
| Arg | Gly | Gly | Pro | Asn | Met | Arg | Met | Ile | Arg | Leu | Asp | Pro | Ser | Lys | Pro | |
| 65 | | | | | 70 | | | | | 75 | | | | | 80 | |
| TCT | CTA | ACG | GTG | ACA | GGA | TAT | ATT | TTC | AAT | AAG | TTT | GTG | CAT | CCT | TAT | 288 |
| Ser | Leu | Thr | Val | Thr | Gly | Tyr | Ile | Phe | Asn | Lys | Phe | Val | His | Pro | Tyr | |
| | | | | 85 | | | | | 90 | | | | | 95 | | |
| GAG | AAC | CGT | TTT | ATT | ACC | GTG | CGT | GAA | GCT | GCA | AGA | CTG | CAA | GGC | TTC | 336 |
| Glu | Asn | Arg | Phe | Ile | Thr | Val | Arg | Glu | Ala | Ala | Arg | Leu | Gln | Gly | Phe | |
| | | | | 100 | | | | | 105 | | | | | 110 | | |
| CCA | GAT | TCA | TTA | AAA | TTT | GAA | GGC | TCA | TTA | ACT | AGT | ACG | CAG | ATG | CAA | 384 |
| Pro | Asp | Ser | Leu | Lys | Phe | Glu | Gly | Ser | Leu | Thr | Ser | Thr | Gln | Met | Gln | |
| | | | 115 | | | | | 120 | | | | | 125 | | | |
| GTC | GGC | AAT | GCC | GTG | CCA | GTA | CAA | TTA | GCT | AAA | GCA | GTT | TTT | GAA | GCG | 432 |
| Val | Gly | Asn | Ala | Val | Pro | Val | Gln | Leu | Ala | Lys | Ala | Val | Phe | Glu | Ala | |
| | | 130 | | | | | 135 | | | | | 140 | | | | |
| GTA | CTA | ATT | TCT | GTT | AGA | AAA | TTA | GGA | TAT | GGC | AAA | AGA | AAT | TTA | ACT | 480 |
| Val | Leu | Ile | Ser | Val | Arg | Lys | Leu | Gly | Tyr | Gly | Lys | Arg | Asn | Leu | Thr | |
| 145 | | | | | 150 | | | | | 155 | | | | | 160 | |
| GCG | TTT | AGT | CTT | TTT | AGC | GGT | GCT | GGT | GGA | CTT | GAT | ATT | GGT | GCT | GAA | 528 |
| Ala | Phe | Ser | Leu | Phe | Ser | Gly | Ala | Gly | Gly | Leu | Asp | Ile | Gly | Ala | Glu | |
| | | | | 165 | | | | | 170 | | | | | 175 | | |
| CAA | GCT | ACA | TAT | AAA | TCA | ATG | AAA | ATA | GAA | ACC | TTG | GTG | ACA | TTA | GAT | 576 |
| Gln | Ala | Thr | Tyr | Lys | Ser | Met | Lys | Ile | Glu | Thr | Leu | Val | Thr | Leu | Asp | |
| | | | 180 | | | | | 185 | | | | | 190 | | | |
| AAT | TGG | AAA | GAC | GCT | TGT | GAT | ACC | CTT | AGA | GGA | TTC | TAT | CAA | GGA | CGT | 624 |
| Asn | Trp | Lys | Asp | Ala | Cys | Asp | Thr | Leu | Arg | Gly | Phe | Tyr | Gln | Gly | Arg | |
| | | 195 | | | | | 200 | | | | | 205 | | | | |
| ACA | AGT | GTT | TTG | CAA | GGA | GAT | ATT | TCA | GAG | ATA | CAA | GAC | CCC | AAA | TTA | 672 |
| Thr | Ser | Val | Leu | Gln | Gly | Asp | Ile | Ser | Glu | Ile | Gln | Asp | Pro | Lys | Leu | |
| 210 | | | | | | 215 | | | | | 220 | | | | | |
| TTA | TGG | CAT | CAA | GAA | TCA | CAA | CAC | GAT | CAG | ATT | CCT | GAT | ATT | GTA | TTT | 720 |
| Leu | Trp | His | Gln | Glu | Ser | Gln | His | Asp | Gln | Ile | Pro | Asp | Ile | Val | Phe | |
| 225 | | | | | 230 | | | | | 235 | | | | | 240 | |
| GGG | GGG | CCT | CCC | TGC | CAG | GCG | TTC | AGT | CAA | GCT | GGT | AAA | CAA | AAG | GCA | 768 |
| Gly | Gly | Pro | Pro | Cys | Gln | Ala | Phe | Ser | Gln | Ala | Gly | Lys | Gln | Lys | Ala | |
| | | | | 245 | | | | | 250 | | | | | 255 | | |
| ACA | AAT | GAC | CCG | AGA | GGA | AAC | TTG | ATT | TAC | GAG | TAC | CTC | AGA | TTT | ATT | 816 |
| Thr | Asn | Asp | Pro | Arg | Gly | Asn | Leu | Ile | Tyr | Glu | Tyr | Leu | Arg | Phe | Ile | |
| | | | 260 | | | | | 265 | | | | | 270 | | | |
| GAG | AAA | ATC | AAC | CCT | CCA | TTC | TTT | GTA | ATG | GAA | AAT | GTA | GCG | AAC | TTG | 864 |
| Glu | Lys | Ile | Asn | Pro | Pro | Phe | Phe | Val | Met | Glu | Asn | Val | Ala | Asn | Leu | |
| | | 275 | | | | | 280 | | | | | 285 | | | | |
| AAA | GGT | GTT | CAG | CGC | GGG | GAA | CTT | TAT | CAA | GAC | ATT | TTG | GAG | CGC | ATG | 912 |
| Lys | Gly | Val | Gln | Arg | Gly | Glu | Leu | Tyr | Gln | Asp | Ile | Leu | Glu | Arg | Met | |
| | 290 | | | | | 295 | | | | | 300 | | | | | |
| TCT | AAT | CTT | GGT | TAT | AAT | GTG | ACG | GTT | GCC | CCG | CTT | CTT | GCG | GCG | GAT | 960 |
| Ser | Asn | Leu | Gly | Tyr | Asn | Val | Thr | Val | Ala | Pro | Leu | Leu | Ala | Ala | Asp | |
| 305 | | | | | 310 | | | | | 315 | | | | | 320 | |
| TAT | GGT | GCA | CCA | CAG | CTT | AGA | AAA | CGT | CTA | ATA | TTC | TTA | GGC | TGT | AA1 | 008 |
| Tyr | Gly | Ala | Pro | Gln | Leu | Arg | Lys | Arg | Leu | Ile | Phe | Leu | Gly | Cys | Lys | |
| | | | | 325 | | | | | 330 | | | | | 335 | | |
| AAG | GAA | TTC | GGG | GTG | ATG | GAA | CTC | CCA | GTT | CCG | ACC | CAT | AGT | AAT | AC1 | 056 |
| Lys | Glu | Phe | Gly | Val | Met | Glu | Leu | Pro | Val | Pro | Thr | His | Ser | Asn | Thr | |
| | | | | 340 | | | | | 345 | | | | | 350 | | |
| CCC | GAT | TTA | TTA | TCA | CCA | AAC | CCT | TAT | GTA | ACA | GTG | GGG | GAA | GCC | TT1 | 104 |
| Pro | Asp | Leu | Leu | Ser | Pro | Asn | Pro | Tyr | Val | Thr | Val | Gly | Glu | Ala | Phe | |
| | | 355 | | | | | 360 | | | | | 365 | | | | |

```
AAA  GGT  TTA  CCT  AAA  CTT  GTT  TAA                                             1128
Lys  Gly  Leu  Pro  Lys  Leu  Val
     370                 375
```

( 2 ) INFORMATION FOR SEQ ID NO:5:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:5:

```
Met  Gly  Glu  Asn  Gln  Glu
 1                 5
```

( 2 ) INFORMATION FOR SEQ ID NO:6:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:6:

```
Asp  Lys  Ala  Gln  Leu  Val
 1                 5
```

( 2 ) INFORMATION FOR SEQ ID NO:7:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
    ( A ) NAME/KEY:
    ( B ) LOCATION: 5
    ( D ) OTHER INFORMATION: N =A, C, G or T
    ( A ) NAME/KEY:
    ( B ) LOCATION: 8 and 14
    ( D ) OTHER INFORMATION: R =A or G
    ( A ) NAME/KEY:
    ( B ) LOCATION: 11

(D) OTHER INFORMATION: Y =C or T (xi) SEQUENCE DESCRIPTION: SEQ ID NO:7:

ATGGNGARAA YCARGA                                                16

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Synthetic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY:
        (B) LOCATION: 9
        (D) OTHER INFORMATION: N =A, C, G or T
        (A) NAME/KEY:
        (B) LOCATION: 15
        (D) OTHER INFORMATION: R =A or G
        (A) NAME/KEY:
        (B) LOCATION: 3, 6, and 12
        (D) OTHER INFORMATION: Y =C or T (xi) SEQUENCE DESCRIPTION: SEQ ID NO:8:

ACYAAYTGNG CYTTRTC                                               17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Synthetic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY:
        (B) LOCATION: 3 and 9
        (D) OTHER INFORMATION: N =A, C, G or T
        (A) NAME/KEY:
        (B) LOCATION: 15
        (D) OTHER INFORMATION: R =A or G
        (A) NAME/KEY:
        (B) LOCATION: 6 and 12
        (D) OTHER INFORMATION: Y =C or T (xi) SEQUENCE DESCRIPTION: SEQ ID NO:9:

ACNAGYTGNG CYTTRTC                                               17

(2) INFORMATION FOR SEQ ID NO:10:

(i) SEQUENCE CHARACTERISTICS:
        (A) LENGTH: 59 base pairs
        (B) TYPE: nucleic acid (C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

```
ATGGGAGAAA ACCAAGAATC AATATGGGCA AATCAGATAT TGGACAAGGC CCAACTGGT            59
```

(2) INFORMATION FOR SEQ ID NO:11:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:11:

```
Met Gly Glu Asn Gln Glu Ser Ile Trp Ala Asn Gln Ile Leu Asp Lys
 1               5                  10                  15
Ala Gln Leu Val
         20
```

(2) INFORMATION FOR SEQ ID NO:12:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: Synthetic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

```
GATATTGGAC AAGGCCCAAC TGGT            24
```

(2) INFORMATION FOR SEQ ID NO:13:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: Synthetic DNA (iii) HYPOTHETICAL: NO -continued ( i v ) ANTI-SENSE: NO ( v ) FRAGMENT TYPE:

( v i ) ORIGINAL SOURCE:

( x i ) SEQUENCE DESCRIPTION: SEQ ID NO:13:

TATTGATTCT TGGTTTCTC CCAT          24

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:14:

TCCGCTAATT ACCTTACCAT TATTGGT          27

( 2 ) INFORMATION FOR SEQ ID NO:15:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:15:

CTTTAACTTC AGCCAATAGC ATTATGT          27

( 2 ) INFORMATION FOR SEQ ID NO:16:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:16:

AGCTCTAGAG GAGGTAAATA AATGGGAGAA AACCAAGAAT CAATATGGGC A          51

( 2 ) INFORMATION FOR SEQ ID NO:17:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:17:

CGCGGATCCT CAGAATTGGA AGTTTCTCT AATCCATTCA TC  42

( 2 ) INFORMATION FOR SEQ ID NO:18:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:18:

TCTTTCGTCG CTCAGGTTCT GAAGTAC  27

( 2 ) INFORMATION FOR SEQ ID NO:19:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:19:

TGATTAAAAA CAAAGTCGAA AGATTCG  27

( 2 ) INFORMATION FOR SEQ ID NO:20:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:20:

GGAAAATGTA GCGAACTTGA AAGGTGT 27

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:21:

ACAAAGAATG GAGGGTTGAT TTTCTCA 27

( 2 ) INFORMATION FOR SEQ ID NO:22:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:22:

CAAGGATCCG GAGGTTAATT AAATGAATGG ATTAGAGAAA ACTTCCAAT 49

( 2 ) INFORMATION FOR SEQ ID NO:23:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:23:

TTCGGATCCT TAAACAAGTT TAGGTAAACC TTTGAAGGC 39